United States Patent
Ryu et al.

(10) Patent No.: US 7,848,821 B1
(45) Date of Patent: Dec. 7, 2010

(54) APPARATUS AND METHOD FOR ELECTRODE INSERTION IN HEART TISSUE

(75) Inventors: Kyungmoo Ryu, Palmdale, CA (US); Gene A. Bornzin, Simi Valley, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 948 days.

(21) Appl. No.: 11/456,825

(22) Filed: Jul. 11, 2006

(51) Int. Cl.
*A61N 1/05* (2006.01)

(52) U.S. Cl. .................. 607/122; 607/126; 607/128

(58) Field of Classification Search .......... 607/40, 607/112–116, 122, 126, 128–132; 600/18, 600/407, 463, 437; 606/41, 129, 191; 604/528, 604/530
See application file for complete search history.

(56) References Cited

U.S. PATENT DOCUMENTS

| | | | |
|---|---|---|---|
| 3,902,501 A | 9/1975 | Citron et al. | |
| 3,974,834 A | 8/1976 | Kane | |
| 4,103,690 A * | 8/1978 | Harris | 607/128 |
| 4,258,724 A * | 3/1981 | Balat et al. | 607/128 |
| 4,378,023 A * | 3/1983 | Trabucco | 607/128 |
| 4,475,560 A | 10/1984 | Tarjan et al. | |
| 4,721,118 A | 1/1988 | Harris | |
| 4,919,135 A | 4/1990 | Phillips, Jr. et al. | |
| 5,251,634 A | 10/1993 | Weinberg | |
| 5,314,462 A * | 5/1994 | Heil et al. | 607/128 |
| 5,395,328 A | 3/1995 | Ockuly et al. | |
| 5,395,329 A | 3/1995 | Fleischhackor et al. | |
| 5,443,492 A * | 8/1995 | Stokes et al. | 607/131 |
| 5,492,119 A * | 2/1996 | Abrams | 600/375 |
| 5,851,227 A * | 12/1998 | Spehr | 607/126 |
| 6,083,216 A * | 7/2000 | Fischer, Sr. | 604/530 |
| 7,072,703 B2 | 7/2006 | Zhang et al. | |
| 7,082,335 B2 | 7/2006 | Klein et al. | |
| 7,184,842 B2 | 2/2007 | Seifert et al. | |
| 7,187,982 B2 | 3/2007 | Seifert et al. | |
| 7,418,298 B2 * | 8/2008 | Shiroff et al. | 607/126 |
| 2002/0103522 A1 * | 8/2002 | Swoyer et al. | 607/116 |
| 2002/0120318 A1 | 8/2002 | Kroll et al. | |
| 2003/0195602 A1 * | 10/2003 | Boling | 607/122 |
| 2004/0088035 A1 | 5/2004 | Guenst et al. | |

(Continued)

FOREIGN PATENT DOCUMENTS

EP    1421913 A1    5/2004

(Continued)

OTHER PUBLICATIONS

NonFinal Office Action, mailed Oct. 19, 2009—Related U.S. Appl. No. 11/832,027.

(Continued)

*Primary Examiner*—Carl H Layno
*Assistant Examiner*—Paula J Stice

(57) ABSTRACT

What is described is a method of implanting one or more electrodes of a pacing or defibrillation lead in heart tissue. The method comprises positioning a distal end of a catheter against a surface of the heart tissue, extending a distal end of a first electrode from a lumen of the catheter such that the distal end of the first electrode penetrates the surface, and retracting the first electrode to fix a hook feature of the first electrode in the heart tissue.

19 Claims, 9 Drawing Sheets

U.S. PATENT DOCUMENTS

| | | |
|---|---|---|
| 2004/0127889 A1 | 7/2004 | Zhang et al. |
| 2004/0230283 A1* | 11/2004 | Prinzen et al. ............... 607/126 |
| 2005/0033395 A1* | 2/2005 | Seifert et al. ................ 607/126 |
| 2005/0065419 A1 | 3/2005 | Partridge et al. |
| 2005/0149138 A1 | 7/2005 | Min et al. |
| 2006/0009831 A1 | 1/2006 | Lau et al. |
| 2006/0020316 A1 | 1/2006 | Martinez et al. |
| 2006/0036307 A1* | 2/2006 | Zarembo et al. ............ 607/122 |
| 2006/0178666 A1* | 8/2006 | Cosman et al. ................ 606/41 |
| 2007/0088417 A1 | 4/2007 | Schouenborg |
| 2007/0106358 A1 | 5/2007 | Westlund et al. |
| 2007/0233217 A1 | 10/2007 | Yang et al. |

FOREIGN PATENT DOCUMENTS

| | | |
|---|---|---|
| EP | 1547648 A1 | 6/2005 |

OTHER PUBLICATIONS

NonFinal Office Action, mailed Apr. 14, 2010—Related U.S. Appl. No. 11/832,027.

Final Office Action, mailed Jul. 29, 2010—Related U.S. Appl. No. 11/832,027.

* cited by examiner

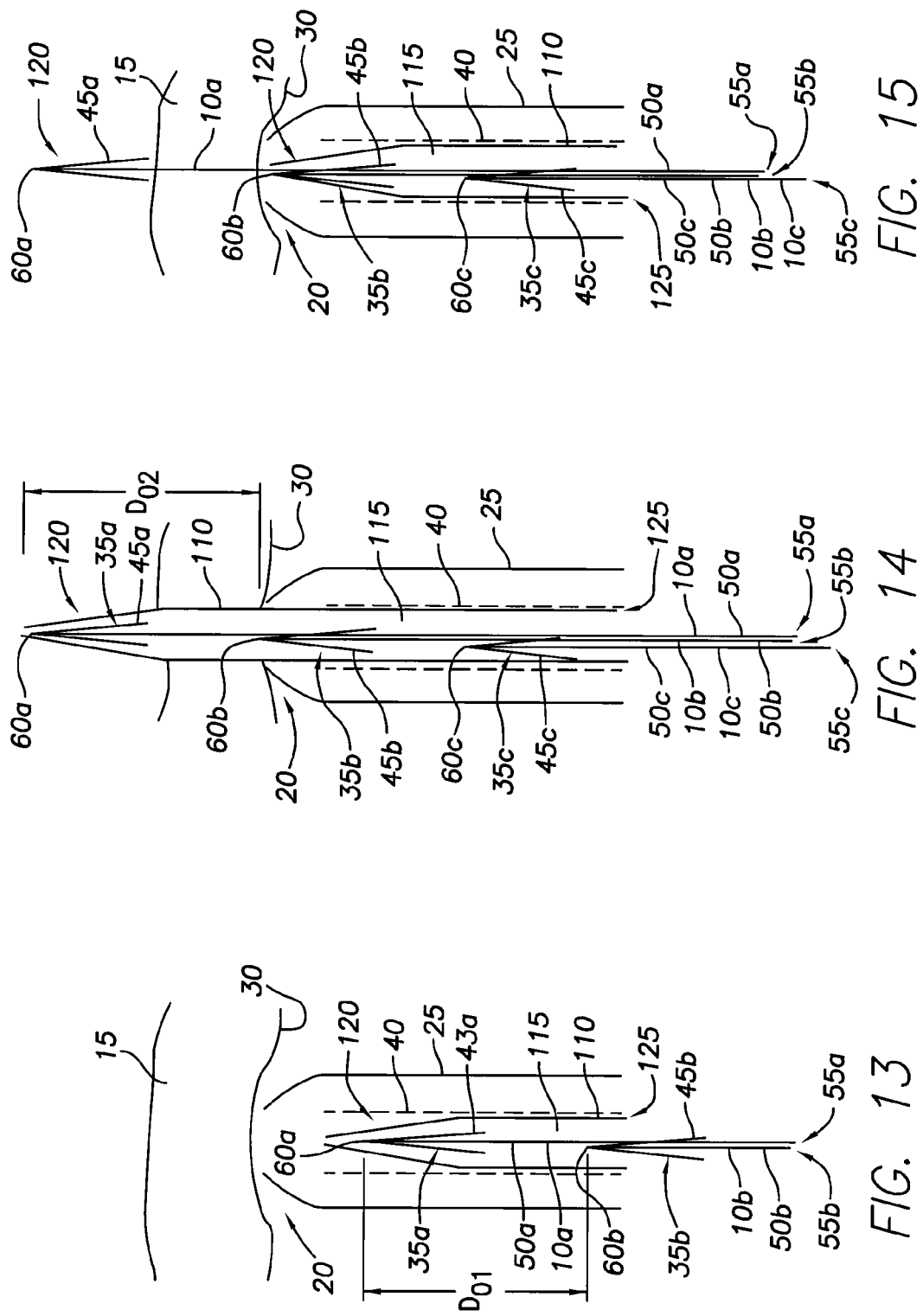

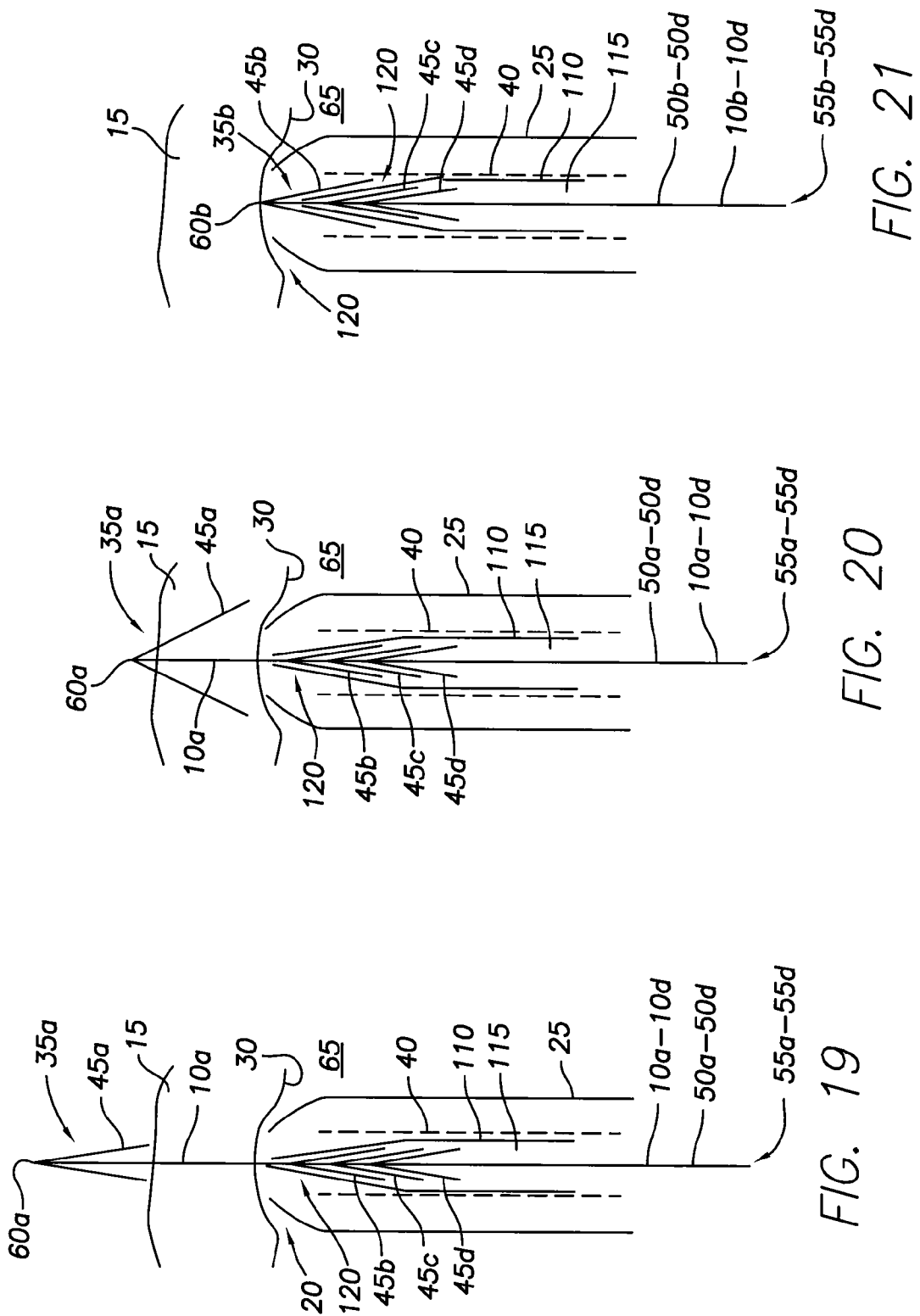

APPARATUS AND METHOD FOR ELECTRODE INSERTION IN HEART TISSUE

FIELD OF THE INVENTION

The present invention relates to medical devices and methods. More specifically, the present invention relates to devices and methods of implanting pacing and defibrillation leads.

BACKGROUND OF THE INVENTION

Intrapericardial lead placement techniques advantageously allow the implantation of leads virtually anywhere on the epicardium of the atria or ventricle to prevent/terminate atrial arrhythmias. Additionally, these techniques provide the opportunity to implant multiple pacing leads for biventricular pacing to optimize pacing efficacy and efficiency.

There is a need in the art for a system and/or device that facilitates fast and easy placement of single or multiple electrodes on one or more locations of the epicardium or endocardium of the heart. There is also a need in the art for a method of that facilitates fast and easy placement of single or multiple electrodes on one or more locations of the epicardium or endocardium of the heart.

BRIEF SUMMARY OF THE INVENTION

The present invention, in one embodiment, is a method of implanting one or more electrodes of a pacing or defibrillation lead in heart tissue. The method comprises positioning a distal end of a catheter against a surface of the heart tissue, extending a distal end of a first electrode from a lumen of the catheter such that the distal end of the first electrode penetrates the surface, and retracting the first electrode to fix a hook feature of the first electrode in the heart tissue.

The present invention, in one embodiment, is an assembly for implanting in heart tissue one or more electrodes of a defibrillation or pacing lead. The assembly comprises a catheter and a first electrode. The catheter comprises a proximal end, a distal end and a lumen extending between the proximal and distal ends. The first electrode is displaceably received in the lumen and comprises a longitudinally extending portion comprising a proximal end and a distal end. The distal end comprises a piercing tip and at least one hook feature. The application of a distally oriented force to the first electrode causes the piercing tip to pierce the heart tissue, and a subsequent application of a proximally oriented force to the first electrode causes the hook feature to become fixed in the heart tissue.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 13 is a diagrammatic representation of a needle in which a series of electrodes are staged within the lumen of the needle, the needle extends through the lumen of the catheter, and the catheter distal end is pushed against the tissue wall of a heart.

FIG. 14 is the same diagrammatic representation as FIG. 13, except the distal end of the needle has pierced the heart tissue wall.

FIG. 15 is the same diagrammatic representation as FIG. 14, except the needle has been retracted to leave the first electrode in the heart tissue wall.

FIG. 19 is the same diagrammatic representation as FIG. 18, except the needle has been retracted to leave the first electrode in the heart tissue wall.

FIG. 20 is the same diagrammatic representation as FIG. 19, except the first electrode has been retracted to set the hook feature in the tissue wall.

FIG. 21 is the same diagrammatic representation as FIG. 20, except the second electrode is now positioned distal of the distal end of the needle to be the next electrode implanted.

DETAILED DESCRIPTION

Figure 3:
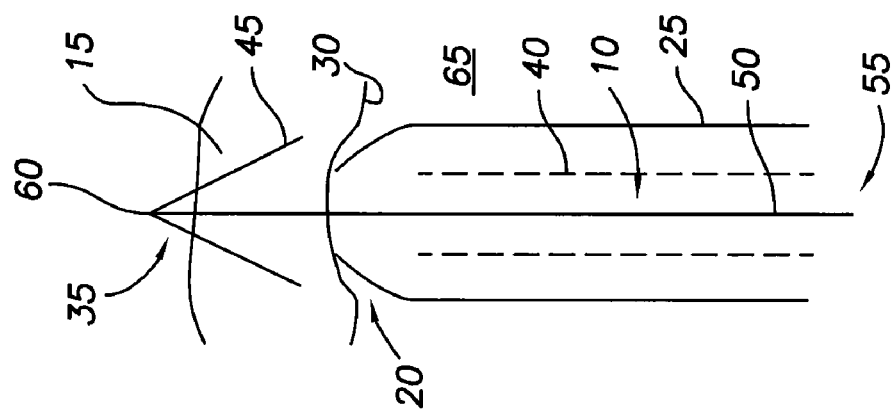
FIG. 3 is the same diagrammatic representation as FIG. 2, except the wire electrode has been retracted to set the hook electrodes in the tissue wall.

Devices and methods of implanting one or more electrodes 10 of a pacing or defibrillation lead in heart tissue 15 are disclosed in this Detailed Description. In one embodiment, the method comprises positioning a distal end 20 of a catheter 25 against a surface 30 of the heart tissue 15, extending a distal end 35 of an electrode 10 from a lumen 40 of the catheter 25 such that the distal end 35 of the electrode 10 penetrates the surface 30, and retracting the electrode 10 to fix a hook feature 45 of the electrode 10 in the heart tissue 15.

Figure 2:
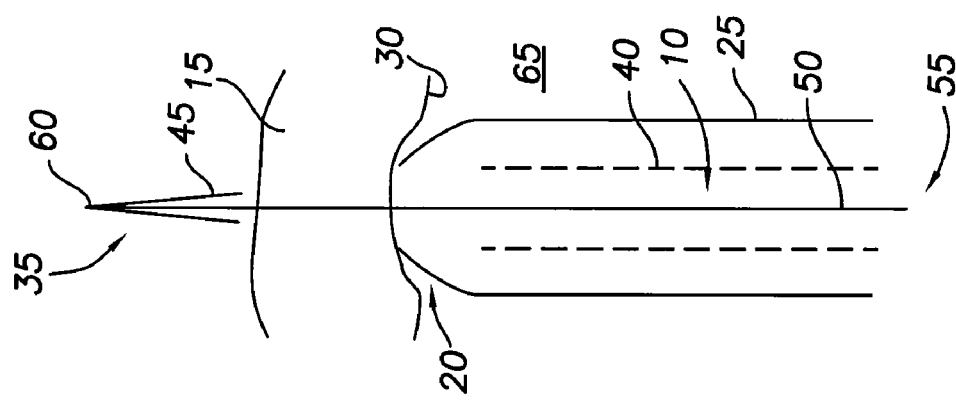
FIG. 2 is the same diagrammatic representation as FIG. 1, except the wire electrode has been inserted into the tissue wall.
Figure 1:
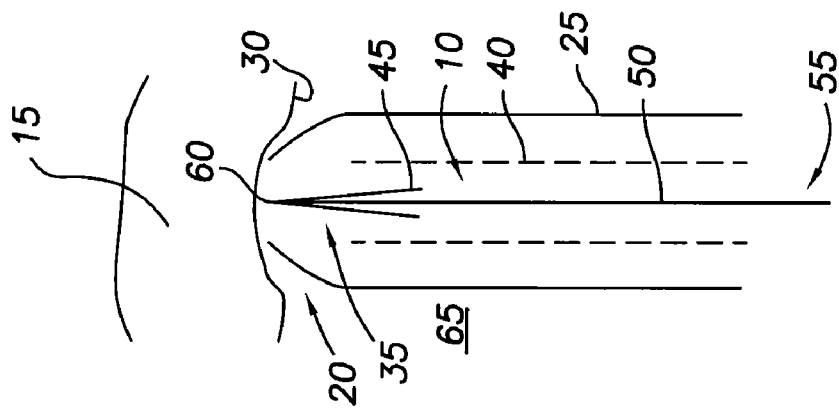
FIG. 1 is a diagrammatic representation of a sufficiently stiff or rigid wire electrode in the lumen of a catheter, wherein the catheter distal end is pushed against the tissue wall of a heart.

For a discussion of a method and device that employ an electrode 10 that is sufficiently stiff or rigid within a lumen 40 of a catheter 25 to allow a distal end 35 of the electrode 10 to be driven through the surface 30 of heart tissue 15 via a distally directed force applied to a proximal end 55 of the electrode 10, reference is made to FIGS. 1-3. FIG. 1 is a diagrammatic representation of a sufficiently stiff or rigid wire electrode 10 in the lumen 40 of a catheter 25, wherein the catheter distal end 20 is pushed against the tissue wall 15 of a heart. FIG. 2 is the same diagrammatic representation as FIG. 1, except the wire electrode 10 has been inserted into the tissue wall 15. FIG. 3 is the same diagrammatic representation as FIG. 2, except the wire electrode 10 has been retracted to set the hook feature 45 in the tissue wall 15.

As depicted in FIGS. 1-3, the electrode 10 includes an insulated body 50, a distal end 35 and a proximal end 55. The distal end 35 includes one or more hook features 45 (e.g., barbs, hooks, etc.) and terminates in a piercing tip 60. In one embodiment, the hook features 45 are uninsulated to allow an electrical current to be communicated to the heart tissue 15 in which the electrode distal end 35 is implanted. The electrode 10 is longitudinally displaceably positioned in the lumen 40 of the catheter 25. The electrode 10, and more specifically, the body 50 is sufficiently supported by the walls of the lumen 40 of the catheter 25 such that a distally directed force can be applied to the proximal end 55 of the electrode 10 without the body 50 undergoing column-type deflection of any significance, thereby causing the distal end 35 of the electrode 10 to penetrate the surface 30 of heart tissue 15. In other words, the body 50 is capable of withstanding a compressive force with little or no column-type deflection. As a result, electrode 10 can be driven into heart tissue 15 via the application of a distally directed force applied to the proximal end 55 of the electrode 10. The electrode's ability to be driven distally via a distally directed force is made possible by a combination of the body's own resistance to column-type deflection and the resistance to column-type deflection provided to the body 50 via the support of the walls of the lumen 40 of the catheter 25 surrounding the body 50 of the electrode 10.

In one embodiment, the diameter of the body 50 of the electrode 10 is less than or equal to approximately three French. In one embodiment, the diameter of the body 50 of the electrode 10 is approximately one French.

As illustrated in FIG. 1, the distal end 20 of the catheter is pushed against the surface 30 of the tissue wall 15 of the heart. In one embodiment, the surface 30 is the epicardium 30 and the catheter distal end 20 approaches the epicardium 30 via the intrapericardial space 65. Examples of devices and methods of accessing the intrapericardial space 65 are provided in U.S. patent application Ser. No. 11/001,374, filed Nov. 30, 2004, and U.S. patent application Ser. No. 11/001,375, filed Nov. 30, 2004, both of which are hereby incorporated by reference in their entireties. In one embodiment, the surface 30 is the endocardium 30 and the catheter distal end 20 approaches the endocardium 30 via the endocardial space 65. In one embodiment, the electrodes 10 are delivered to the endocardial and pericardial spaces via steerable electrophysiology catheters. Examples of such catheters and methods of accessing the endocardial and pericardial spaces are provided in U.S. Pat. No. 5,395,328 to Ockuly, et al. and U.S. Pat. No. 5,395,329 to Fleischhacker, et al., both of which issued Mar. 7, 1995 are hereby incorporated by reference in their entireties.

As shown in FIG. 2, once the distal end 20 of the catheter 25 is positioned against the surface 30 of the heart tissue wall 15, a distally oriented force is exerted against the electrode proximal end 55. Because of the electrode body 50 is sufficiently stiff or rigid, the distally oriented force causes the electrode 10 to distally displace in the lumen 40, which causes the electrode distal end 35 to extend from the catheter lumen 40 and into the heart tissue wall 15 via the piercing tip 60.

As shown in FIG. 3, once the electrode distal end 35 has pierced the heart tissue wall 15 a sufficient distance, a proximally oriented force is applied to the electrode proximal end 55. The proximally oriented force proximally displaces the electrode 10 within the catheter lumen 40, which partially retracts the electrode distal end 35 and causes the hook feature (s) 45 to imbed in the heart tissue wall 15. As a result, the electrode distal end 35 is fixed to the heart wall tissue 15.

Figure 6:
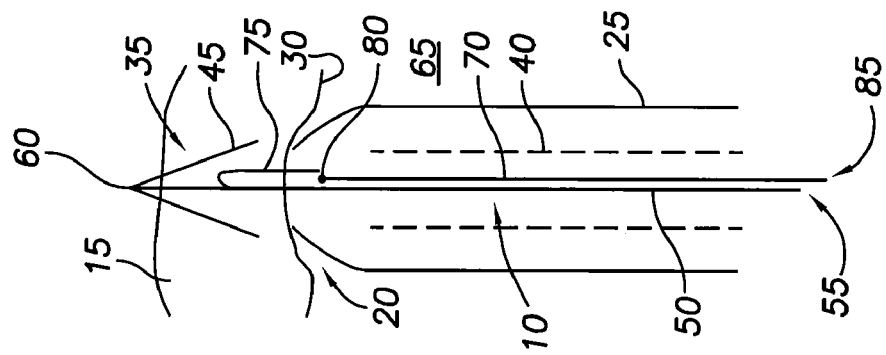
FIG. 6 is the same diagrammatic representation as FIG. 5, except the electrode has been retracted to set the hook feature in the tissue wall.
Figure 5:
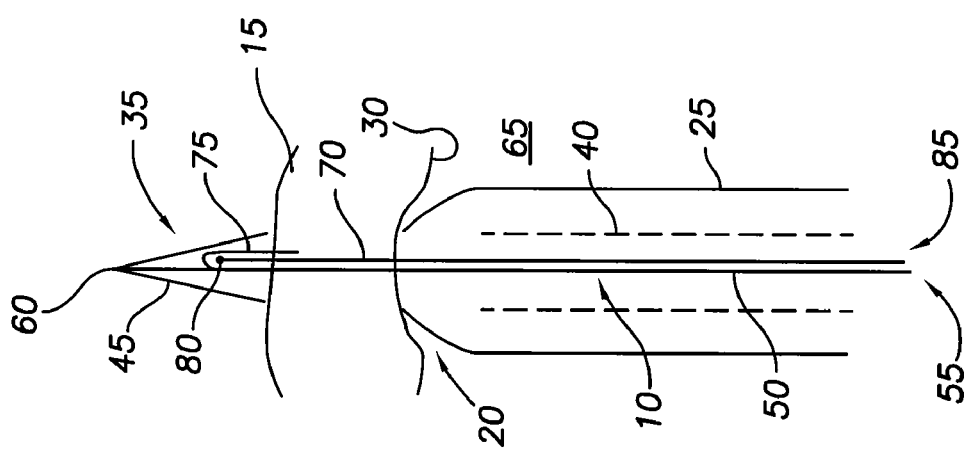
FIG. 5 is the same diagrammatic representation as FIG. 4, except the distal urging of the push rod has caused the electrode to pierce the heart tissue wall.
Figure 4:
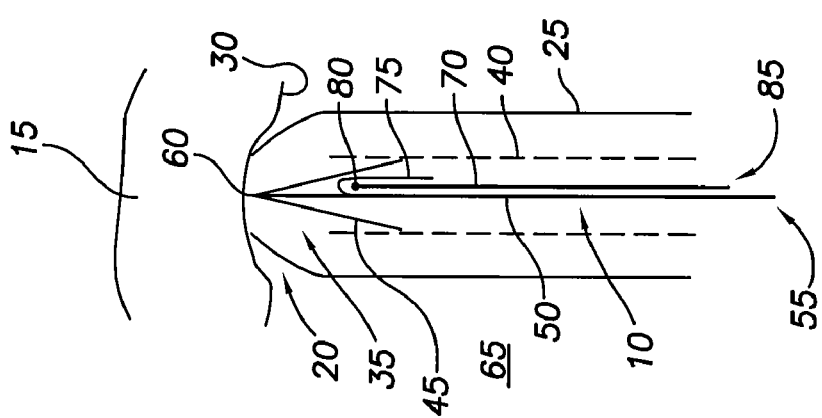
FIG. 4 is a diagrammatic representation of a push rod acting on a feature of the electrode, wherein the electrode extends through the lumen of a catheter having a distal end pushed against the tissue wall of a heart.

For a discussion of a method and device that employ a push rod 70 acting on a feature 75 of the electrode 10 to distally displace the electrode 10, reference is made to FIGS. 4-6. FIG. 4 is a diagrammatic representation of a push rod 70 acting on a feature 75 of the electrode 10, wherein the electrode 10 extends through the lumen 40 of a catheter 25 having a distal end 20 pushed against the tissue wall 15 of a heart. FIG. 5 is the same diagrammatic representation as FIG. 4, except the distal urging of the push rod 70 has caused the electrode 10 to pierce the heart tissue wall 15. FIG. 6 is the same diagrammatic representation as FIG. 5, except the electrode 10 has been retracted to set the hook feature 45 in the tissue wall 15.

As depicted in FIGS. 4-6, the electrode 10 includes an insulated body 50, a distal end 35 and a proximal end 55. The distal end 35 includes one or more hook features 45 (e.g., barbs, hooks, etc.), a push rod receiving feature 75, and terminates in a piercing tip 60. In one embodiment, the hook features 45 are uninsulated to allow an electrical current to be communicated to the heart tissue 15 in which the electrode distal end 35 is implanted. The electrode is longitudinally displaceably positioned in the lumen 40 of the catheter 25.

In one embodiment, the diameter of the body 50 of the electrode 10 is less than or equal to approximately three French. In one embodiment, the diameter of the body 50 of the electrode 10 is approximately one French.

The push rod 70 includes a distal end 80, a proximal end 85 and is longitudinally displaceably positioned in the catheter lumen 40 adjacent the electrode 10. The push rod distal end 80 is received in the push rod receiving feature 75 of the electrode 10.

As illustrated in FIG. 4, the distal end 20 of the catheter is pushed against the surface 30 of the tissue wall 15 of the heart. In one embodiment, the surface 30 is the epicardium 30 and the catheter distal end 20 approaches the epicardium 30 via the intrapericardial space 65. In one embodiment, the surface 30 is the endocardium 30 and the catheter distal end 20 approaches the endocardium 30 via the endocardial space 65.

As shown in FIG. 5, once the distal end 20 of the catheter 25 is positioned against the surface 30 of the heart tissue wall 15, a distally oriented force is exerted against the push rod proximal end 85. Because the push rod distal end 80 is received in the push rod receiving feature 75 of the electrode 10, the distally oriented force causes the push rod 70 and electrode 10 to distally displace in the lumen 40, which causes the electrode distal end 35 to extend from the catheter lumen 40 and into the heart tissue wall 15 via the piercing tip 60.

As shown in FIG. 6, in one embodiment, once the electrode distal end 35 has pierced the heart tissue wall 15 a sufficient distance, a proximally oriented force is applied to the push rod proximal end 85. The proximally oriented force proximally displaces the push rod 70, which causes the push rod distal end 80 to withdraw from the electrode feature 75. A proximally oriented force is then applied to the electrode proximal end 55, which causes the electrode 10 to proximally displace within the catheter lumen 40. The proximal displacement of the electrode 10 partially retracts the electrode distal end 35 and causes the hook feature(s) 45 to imbed in the heart tissue wall 15. As a result, the electrode distal end 35 is fixed to the heart wall tissue 15.

Alternatively, in one embodiment, as the push rod 70 is retracted after the electrode 10 has sufficiently pierced the heart tissue wall 15, the electrode 10 is retracted with it due to an interference fit between the push rod distal end 80 and the push rod receiving feature 75 on the electrode 10. As a result, the hook feature(s) 45 are caused to imbed in the heart tissue wall 15. Once the hook feature(s) 45 are sufficiently imbedded, further proximal displacement of the push rod 70 causes the push rod 70 to displace proximally relative to the electrode 10, thereby exiting the heart tissue 15, disconnecting from the push rod receiving feature 75 and leaving the electrode 10 behind.

Figure 9:
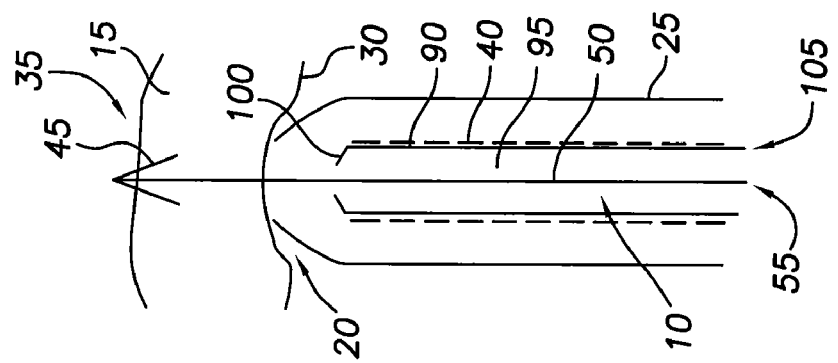
FIG. 9 is the same diagrammatic representation as FIG. 8, except the electrode has been retracted to set the hook feature in the tissue wall.
Figure 8:
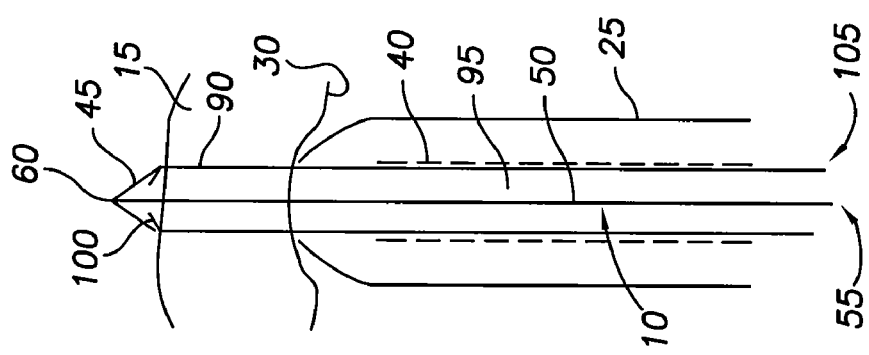
FIG. 8 is the same diagrammatic representation as FIG. 7, except the distal urging of the push tube has caused the electrode to pierce the heart tissue wall.
Figure 7:
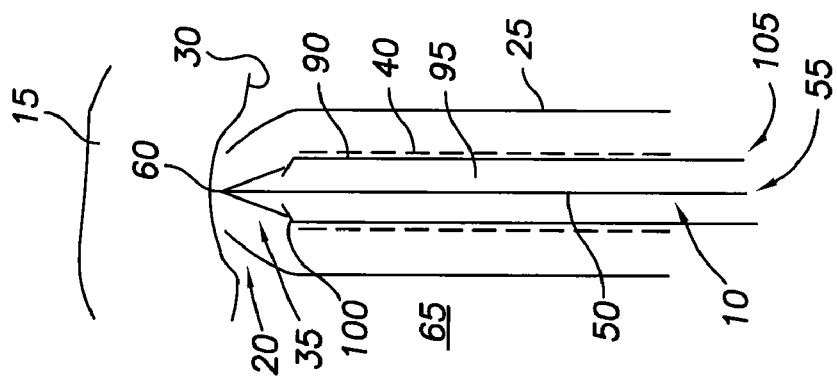
FIG. 7 is a diagrammatic representation of a push tube acting on a feature of the electrode, wherein the electrode extends through a lumen of the push tube, the push tube extends through the lumen of the catheter, and the catheter distal end is pushed against the tissue wall of a heart.

For a discussion of a method and device that employ a push tube 90 acting on a feature of the electrode 10 to distally displace the electrode 10, reference is made to FIGS. 7-9. FIG. 7 is a diagrammatic representation of a push tube 90 acting on a feature of the electrode 10, wherein the electrode 10 extends through a lumen 95 of the push tube 90, the push tube 90 extends through the lumen 40 of the catheter 25, and the catheter distal end 20 is pushed against the tissue wall 15 of a heart. FIG. 8 is the same diagrammatic representation as FIG. 7, except the distal urging of the push tube 90 has caused the electrode 10 to pierce the heart tissue wall 15. FIG. 9 is the same diagrammatic representation as FIG. 8, except the electrode 10 has been retracted to set the hook feature 45 in the tissue wall 15.

As depicted in FIGS. 7-9, the electrode 10 includes an insulated body 50, a distal end 35 and a proximal end 55. The distal end 35 includes one or more hook features 45 (e.g., barbs, hooks, etc.) and terminates in a piercing tip 60. In one embodiment, the hook features 45 are uninsulated to allow an electrical current to be communicated to the heart tissue 15 in which the electrode distal end 35 is implanted.

In one embodiment, the diameter of the body 50 of the electrode 10 is less than or equal to approximately three French. In one embodiment, the diameter of the body 50 of the electrode 10 is approximately one French.

The push tube 90 includes a lumen 95, a distal end 100 and a proximal end 105. The electrode 10 is longitudinally displaceably positioned in the lumen 95 of the push tube 90, and the push tube 90 is longitudinally displaceably positioned in the lumen 40 of the catheter 25. The distal end 100 of the push tube 90 abuts against a feature of the electrode 10. In one embodiment, as shown in FIGS. 7 and 8, the feature is the proximal side of one or more of the hook features 45.

As illustrated in FIG. 7, the distal end 20 of the catheter is pushed against the surface 30 of the tissue wall 15 of the heart. In one embodiment, the surface 30 is the epicardium 30 and the catheter distal end 20 approaches the epicardium 30 via the intrapericardial space 65. In one embodiment, the surface 30 is the endocardium 30 and the catheter distal end 20 approaches the endocardium 30 via the endocardial space 65.

As shown in FIG. 8, once the distal end 20 of the catheter 25 is positioned against the surface 30 of the heart tissue wall 15, a distally oriented force is exerted against the push tube proximal end 105. Because the push tube distal end 100 engages a feature (e.g., one or more of the hook features 45) of the electrode 10, the distally oriented force causes the push tube 90 and electrode 10 to distally displace in the catheter lumen 40, which causes the electrode distal end 35 to extend from the catheter lumen 40 and into the heart tissue wall 15 via the piercing tip 60.

As shown in FIG. 9, in one embodiment, once the electrode distal end 35 has pierced the heart tissue wall 15 a sufficient distance, a proximally oriented force is applied to the push tube proximal end 105. The proximally oriented force proximally displaces the push tube 90, which causes the push tube distal end 100 to withdraw from the electrode feature (e.g., the proximal side of the one or more hook features 45). A proximally oriented force is then applied to the electrode proximal end 55, which causes the electrode 10 to proximally displace within the push tube lumen 95. The proximal displacement of the electrode 10 partially retracts the electrode distal end 35 and causes the hook feature(s) 45 to imbed in the heart tissue wall 15. As a result, the electrode distal end 35 is fixed to the heart wall tissue 15.

Alternatively, in one embodiment, as the push tube 90 is retracted after the electrode 10 has sufficiently pierced the heart tissue wall 15, the electrode 10 is retracted with the push tube 90 due to engagement between the push tube 90 and the electrode 10 (e.g., a friction fit). As a result, the hook feature(s) 45 are caused to imbed in the heart tissue wall 15. Once the hook feature(s) 45 are sufficiently imbedded, further proximal displacement of the push tube 90 causes the push tube 90 to disengage from the electrode 10 and displace proximally relative to the electrode 10, thereby exiting the heart tissue 15 and leaving the electrode 10 behind.

Figure 12:
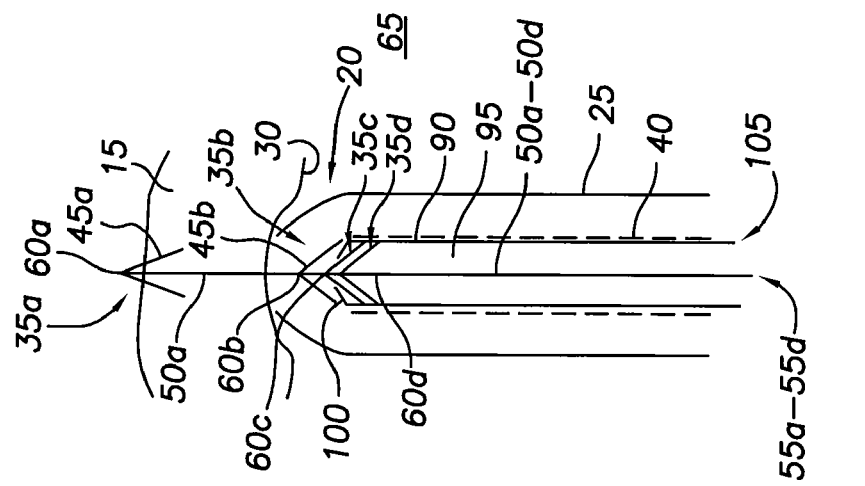
FIG. 12 is the same diagrammatic representation as FIG. 11, except the first electrode has been retracted to set the hook feature in the tissue wall, and the push tube is acting on a feature of the second electrode of the series of electrodes staged in the lumen of the push tube.
Figure 11:
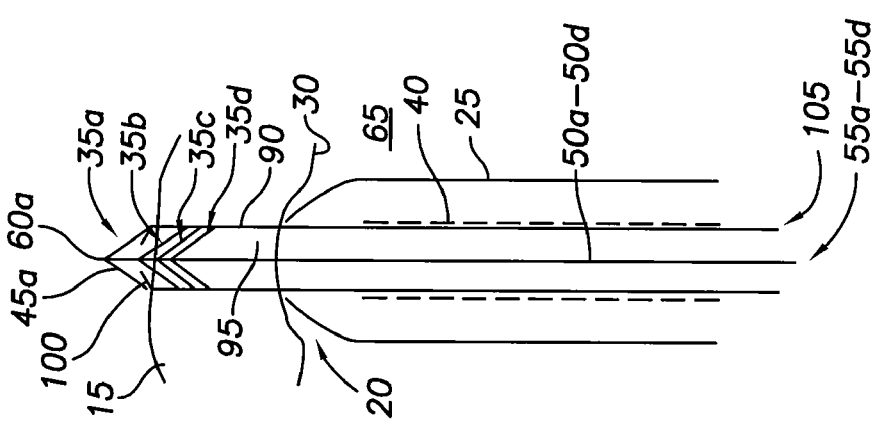
FIG. 11 is the same diagrammatic representation as FIG. 10, except the distal urging of the push tube has caused the first electrode to pierce the heart tissue wall.
Figure 10:
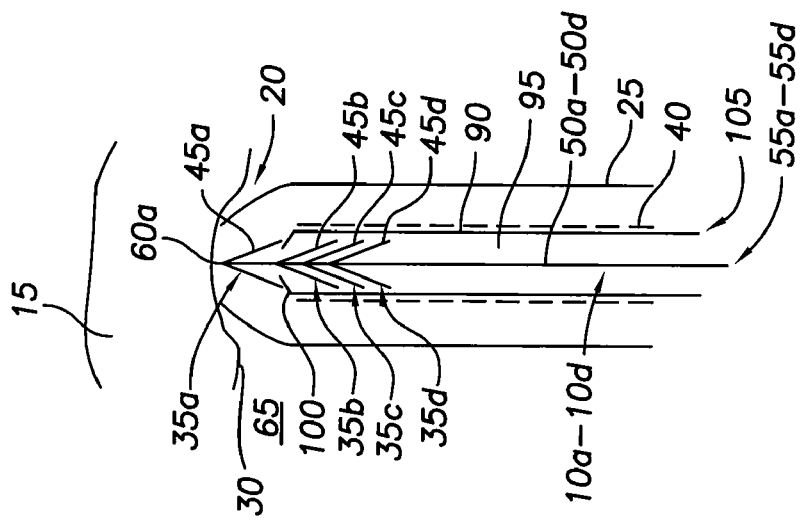
FIG. 10 is a diagrammatic representation of a push tube acting on a feature of a first electrode, wherein a series of electrodes are staged within the lumen of the push tube, the push tube extends through the lumen of the catheter, and the catheter distal end is pushed against the tissue wall of a heart.

For a discussion regarding an alternative version of the embodiment depicted in FIGS. 7-9, wherein a series of electrodes 10a, 10b, 10c, 10d are staged within the lumen 95 of the push tube 90 for implantation at different locations in the heart tissue wall 15 for biventricular pacing, reference is made to FIGS. 10-12. FIG. 10 is a diagrammatic representation of a push tube 90 acting on a feature of a first electrode 10a, wherein a series of electrodes 10a, 10b, 10c, 10d are staged within the lumen 95 of the push tube 90, the push tube 90 extends through the lumen 40 of the catheter 25, and the catheter distal end 20 is pushed against the tissue wall 15 of a heart. FIG. 11 is the same diagrammatic representation as FIG. 10, except the distal urging of the push tube 90 has caused the first electrode 10a to pierce the heart tissue wall 15. FIG. 12 is the same diagrammatic representation as FIG. 11, except the first electrode 10 has been retracted to set the hook feature 45 in the tissue wall 15, and the push tube 90 is acting on a feature of the second electrode 10b of the series of electrodes staged in the lumen 95 of the push tube 90.

As can be understood from FIGS. 10-12, each electrode 10a, 10b, 10c, 10d includes an insulated body 50a, 50b, 50c, 50d, a distal end 35a, 35b, 35c, 35d and a proximal end 55a, 55b, 55c, 55d. Each distal end 35a-35d includes one or more hook features 45a, 45b, 45c, 45d (e.g., barbs, hooks, etc.) and terminates in a piercing tip 60a, 60b, 60c, 60d. In one embodiment, the hook features 45a-45d are uninsulated to allow an electrical current to be communicated to the heart tissue 15 in which the electrode distal end 35a-35d is implanted.

In one embodiment, the diameter of the body 50a, 50b, 50c, 50d of each electrode 10a, 10b, 10c, 10d is less than or equal to approximately three French. In one embodiment, the diameter of the body 50a, 50b, 50c, 50d of each electrode 10a, 10b, 10c, 10d is approximately one French.

The push tube 90 includes a lumen 95, a distal end 100 and a proximal end 105. The electrodes 10a, 10b, 10c, 10d are staged within the lumen 95 of the push tube 90 in a series arrangement such that the distal end 35a of the first or leading electrode 10a is the most distally positioned, respectively followed by the distal ends 35b, 35c, 35d of the second, third and fourth electrodes 10b, 10c, 10d. Accordingly, the electrodes 10a-10d are positioned within the lumen 95 of the push tube 90 such that the electrodes 10a-10d can be implanted in different locations along the surface 30 of the heart wall tissue 15 in the order of their series staging arrangement in the lumen 95 of the push tube 90. While four electrodes 10a-10d are depicted in FIGS. 10-12 as being staged within the lumen 95 of the push tube 90, in other embodiments a greater or lesser number of electrodes 35 will be staged within the lumen 95.

Each electrode 10a-10d is longitudinally displaceably positioned in the lumen 95 of the push tube 90. More specifically, as will be discussed later in this Detailed Description with respect to FIGS. 25 and 26, in one embodiment, the electrodes 10a-10d are adapted to displace distally as a group with the push tube 90, but are adapted such that the push tube 90 and the non-implanted electrodes 10b-10d can be proximally displaced as a group while leaving behind the implanted electrode 10a. The push tube 90 is longitudinally displaceably positioned in the lumen 40 of the catheter 25.

As depicted in FIG. 10, the distal end 100 of the push tube 90 abuts against a feature of the first electrode 10a. In one embodiment, the first electrode 10a is positioned distal of the distal end 100 of the push tube 90 and the feature is the proximal side of one or more of the hook features 45a of the distal end 35a of the first electrode 10a. The remaining staged electrodes 10b-10d are located proximal of the distal end 100 of the push tube 90.

As illustrated in FIG. 10, the distal end 20 of the catheter is pushed against the surface 30 of the tissue wall 15 of the heart. In one embodiment, the surface 30 is the epicardium 30 and the catheter distal end 20 approaches the epicardium 30 via the intrapericardial space 65. In one embodiment, the surface 30 is the endocardium 30 and the catheter distal end 20 approaches the endocardium 30 via the endocardial space 65.

As shown in FIG. 11, once the distal end 20 of the catheter 25 is positioned against the surface 30 of the heart tissue wall 15, a distally oriented force is exerted against the push tube proximal end 105. Because the push tube distal end 100 engages a feature (e.g., one or more of the hook features 45a) of the first electrode 10a and because the electrodes 10a-10d are adapted to displace distally as a group with the push tube 90, the distally oriented force causes the push tube 90 and the electrodes 10a-10d to distally displace in the catheter lumen 40, which causes the electrode distal end 35a of the first or leading electrode 10a to extend from the catheter lumen 40 and into the heart tissue wall 15 via the piercing tip 60a.

As shown in FIG. 12, in one embodiment, once the distal end 35a of the first or leading electrode 10a has pierced the heart tissue wall 15 a sufficient distance, a proximally oriented force is applied to the push tube proximal end 105. The proximally oriented force proximally displaces the push tube 90, which causes the push tube distal end 100 to withdraw from the electrode feature (e.g., the proximal side of the one or more hook features 45a) of the first electrode 10a. As the push tube 90 is retracted after the first electrode 10a has sufficiently pierced the heart tissue wall 15, the first electrode 10 is retracted with the push tube 90. As a result, the hook feature(s) 45a of the first electrode 10a are caused to imbed in the heart tissue wall 15. Once the hook feature(s) 45 are sufficiently imbedded, further proximal displacement of the push tube 90 causes the push tube 90 and the remaining non-implanted electrodes 10b-10d to displace proximally relative to the first electrode 10a, thereby exiting the heart tissue 15 and leaving the first electrode 10 behind.

As shown in FIG. 12, once the push tube 90 is fully retracted proximally with the non-implanted electrodes 10b-10d, a distally oriented force is applied to the proximal ends 55b-55d of the remaining non-implanted electrodes 10b-10d to cause the non-implanted electrodes 10b-10d to displace distally within the lumen 95 of the push tube 90 until the distal end 35b of the second electrode 10b becomes positioned distal to the distal end 100 of the push tube 100. As a result, the push tube 90 is now ready to implant the second electrode 10b, and the catheter distal end 20 is placed against the surface 30 of the heart wall tissue 15 at a second electrode implantation location. The process is then repeated to implant the second electrode 10b in the second electrode implantation location. The process continues to be repeated as necessary until each of the electrodes 10a-10d is implanted in its respective implantation location in the heart tissue wall 15 to achieve an electrode implant arrangement that facilitates biventricular pacing.

Figure 16:
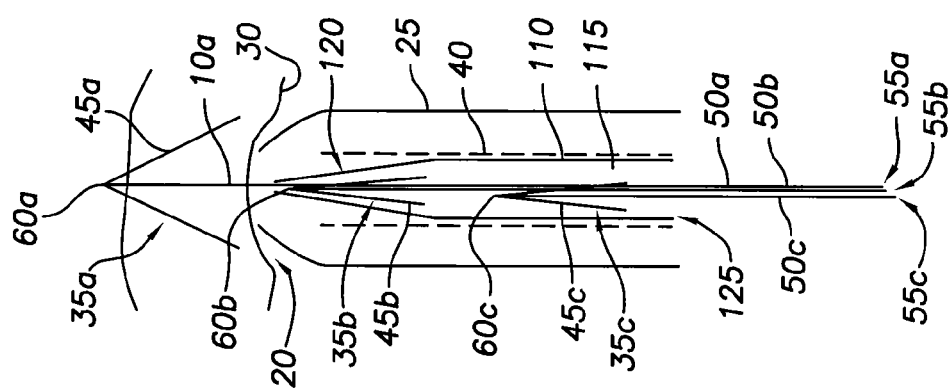
FIG. 16 is the same diagrammatic representation as FIG. 15, except the first electrode has been retracted to set the hook feature in the tissue wall, and the second electrode is now positioned within the distal end of the needle to be the next electrode implanted.

For a discussion of a method and device that employ a needle 110 to implant a series of electrodes 10a, 10b, 10c staged within the lumen 115 of the needle 110 for implantation at different locations in the heart tissue wall 15 for biventricular pacing, reference is made to FIGS. 13-16. FIG. 13 is a diagrammatic representation of a needle 110 in which a series of electrodes 10a, 10b, 10c are staged within the lumen 115 of the needle 110, the needle 110 extends through the lumen 40 of the catheter 25, and the catheter distal end 20 is pushed against the tissue wall 15 of a heart. FIG. 14 is the same diagrammatic representation as FIG. 13, except the distal end 120 of the needle has pierced the heart tissue wall 15. FIG. 15 is the same diagrammatic representation as FIG. 14, except the needle 110 has been retracted to leave the first electrode 10a in the heart tissue wall 15. FIG. 16 is the same diagrammatic representation as FIG. 15, except the first electrode 10a has been retracted to set the hook feature 45a in the tissue wall 15, and the second electrode 10b is now positioned within the distal end 120 of the needle to be the next electrode implanted.

As can be understood from FIGS. 13-16, each electrode 10a, 10b, 10c includes an insulated body 50a, 50b, 50c a distal end 35a, 35b, 35c and a proximal end 55a, 55b, 55c. Each distal end 35a-35c includes one or more hook features 45a, 45b, 45c (e.g., barbs, hooks, etc.) and terminates in a piercing tip 60a, 60b, 60c. In one embodiment, the hook features 45a-45c are uninsulated to allow an electrical current to be communicated to the heart tissue 15 in which the electrode distal end 35a-35c is implanted.

In one embodiment, the diameter of the body 50a, 50b, 50c of each electrode 10a, 10b, 10c is less than or equal to approximately three French. In one embodiment, the diameter of the body 50a, 50b, 50c of each electrode 10a, 10b, 10c is approximately one French.

The needle 110 includes a lumen 115, a distal end 120 and a proximal end 125. The electrodes 10a, 10b, 10c are staged within the lumen 115 of the needle 110 in a series arrangement such that the distal end 35a of the first or leading electrode 10a is the most distally positioned, respectively followed by the distal ends 35b, 35c of the second and third electrodes 10b, 10c. Accordingly, the electrodes 10a-10c are positioned within the lumen 115 of the needle 110 such that the electrodes 10a-10c can be implanted in different locations along the surface 30 of the heart wall tissue 15 in the order of their series staging arrangement in the lumen 115 of the needle 110. While three electrodes 10a-10c are depicted in FIGS. 13-16 as being staged within the lumen 115 of the needle 110, in other embodiments a greater or lesser number of electrodes 35 will be staged within the lumen 115.

Each electrode 10a-10c is longitudinally displaceably positioned in the lumen 115 of the needle 110. The electrodes 10a-10c are adapted to displace distally as a group with the needle 110, and the needle 110 is adapted to displace proximally without causing the electrodes 10a-10c to displace. Thus, once the leading or first electrode 10a is implanted, the needle 110 can be retracted and the second electrode 10b becomes positioned within the distal end 120 of the needle 110 to be implanted next. The needle 110 is longitudinally displaceably positioned in the lumen 40 of the catheter 25.

As depicted in FIG. 13, the distal end 120 of the needle 110 contains the distal end 35a of the first electrode 10a. The remaining staged electrodes 10b-10c are located proximal of the distal end 120 of the needle 110. In one embodiment, the offset distance DO1 between the piercing tip 60a of the first electrode 10a and the piercing tip 60b of the second electrode 10b is approximately equal to the offset distance DO2 between the distal tip of the catheter 25 and the distal tip of the needle 110 when the needle 110 is extended from the catheter 25. Thus, as can be understood from FIGS. 13-16, the distal ends 35a, 35b, 35c are offset from each other by approximately the distance the needle 110 can distally displace out of the catheter distal end 20.

As illustrated in FIG. 13, the distal end 20 of the catheter is pushed against the surface 30 of the tissue wall 15 of the heart. In one embodiment, the surface 30 is the epicardium 30 and the catheter distal end 20 approaches the epicardium 30 via the intrapericardial space 65. In one embodiment, the surface 30 is the endocardium 30 and the catheter distal end 20 approaches the endocardium 30 via the endocardial space 65.

As shown in FIG. 14, once the distal end 20 of the catheter 25 is positioned against the surface 30 of the heart tissue wall 15, a distally oriented force is exerted against needle proximal end 125. As a result, the distal end 120 of the needle 110 extends from the catheter 25 to pierce the heart tissue wall 15. Because the electrodes 10a-10c are adapted to displace distally as a group with the needle 110, the electrodes 10a-10c travel distally with the needle 110, maintaining their positions relative to each other and the needle 110. As the distal end 35a of the first electrode 10a is positioned within the distal end 120 of the needle 110 and the needle distal end 120 has pierced the heart tissue wall 15, the first electrode 10a is also located within the heart tissue wall 15, as depicted in FIG. 14.

As shown in FIG. 15, in one embodiment, once the distal end 35a of the first or leading electrode 10a has sufficiently entered the heart tissue wall 15 via the needle distal end 120, a proximally oriented force is applied to the needle proximal end 125. The proximally oriented force proximally displaces the needle 110, which causes the needle distal end 110 to withdraw from the heart tissue wall 15, leaving behind in the heart tissue wall 15 the distal end 35a of the first electrode and positioning the distal end 35b of the second electrode 10b in the needle distal end 120.

As illustrated in FIG. 16, the first electrode 10a is retracted to cause the hook feature(s) 45a to become fixed in the heart tissue wall 15 once the distal end 35a of the leading or first electrode 10 is left behind in the heart tissue wall 15, the needle 110 is fully retracted, and the distal end 35b of the second electrode 10b is positioned in the needle distal end 120. In one embodiment, to retract the first electrode 10a to set the hook feature(s) 45a in the heart tissue wall 15, the displacement arrangement between the electrodes 10a-10c is similar to that discussed later in this Detailed Description with respect to FIGS. 25 and 26. In other words, the electrodes 10a-10c are distally displaceable as a group, but capable of having an electrode 10a-10c displaced proximally relative to the rest of the electrodes 10a-10c.

As shown in FIG. 16, with the distal end 35a of the first electrode 10a imbedded in the heart tissue wall 15 and the distal end 35b of the second electrode 35b positioned within the distal end 120 of the needle 110, the needle 110 is now ready to implant the second electrode 10b, and the catheter distal end 20 is placed against the surface 30 of the heart wall tissue 15 at a second electrode implantation location. The process is then repeated to implant the second electrode 10b in the second electrode implantation location. The process continues to be repeated as necessary until each of the electrodes 10a-10c is implanted in its respective implantation location in the heart tissue wall 15 to achieve an electrode implant arrangement that facilitates biventricular pacing.

Figure 18:
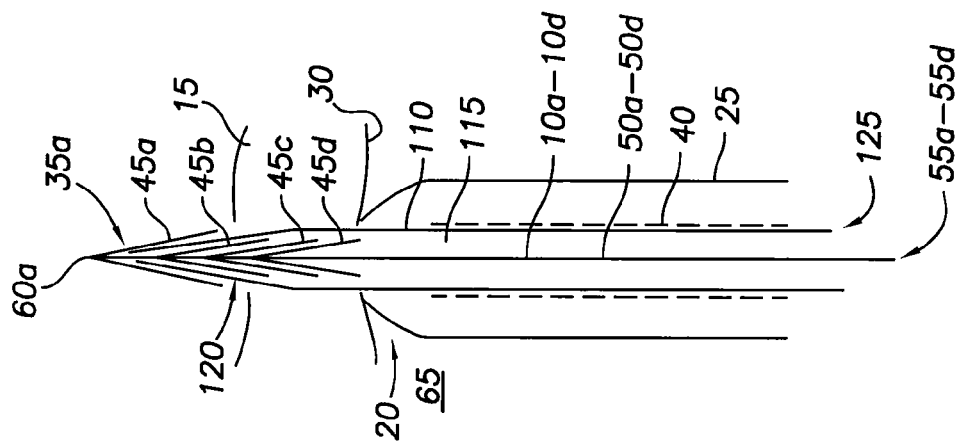
FIG. 18 is the same diagrammatic representation as FIG. 17, except the distal end of the needle has caused the leading or first electrode to pierce the heart tissue wall.
Figure 17:
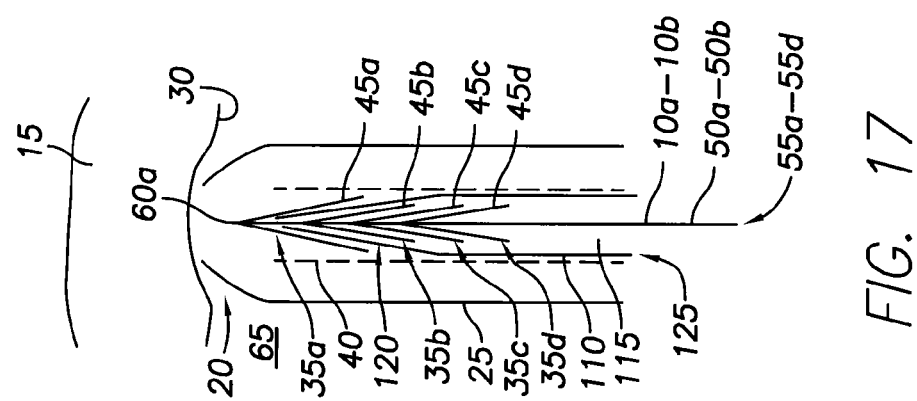
FIG. 17 is a diagrammatic representation of a needle in which a series of electrodes are staged within the lumen of the needle, the needle extends through the lumen of the catheter, and the catheter distal end is pushed against the tissue wall of a heart.

For a discussion of another method and device that employ a needle 110 to implant a series of electrodes 10a, 10b, 10c, 10d staged within the lumen 115 of the needle 110 for implantation at different locations in the heart tissue wall 15 for biventricular pacing, reference is made to FIGS. 17-21. FIG. 17 is a diagrammatic representation of a needle 110 in which a series of electrodes 10a, 10b, 10c, 10d are staged within the lumen 115 of the needle 110, the needle 110 extends through the lumen 40 of the catheter 25, and the catheter distal end 20 is pushed against the tissue wall 15 of a heart. FIG. 18 is the same diagrammatic representation as FIG. 17, except the distal end 120 of the needle has caused the leading or first electrode to pierce the heart tissue wall 15. FIG. 19 is the same diagrammatic representation as FIG. 18, except the needle 110 has been retracted to leave the first electrode 10a in the heart tissue wall 15. FIG. 20 is the same diagrammatic representation as FIG. 19, except the first electrode 10a has been retracted to set the hook feature 45a in the tissue wall 15. FIG. 21 is the same diagrammatic representation as FIG. 20, except the second electrode 10b is now positioned distal of the distal end 120 of the needle to be the next electrode implanted.

As can be understood from FIGS. 17-21, each electrode 10a, 10b, 10c, 10d includes an insulated body 50a, 50b, 50c, 50d, a distal end 35a, 35b, 35c, 35d and a proximal end 55a, 55b, 55c, 55d. Each distal end 35a-35d includes one or more hook features 45a, 45b, 45c, 45d (e.g., barbs, hooks, etc.) and terminates in a piercing tip 60a, 60b, 60c, 60d. In one embodiment, the hook features 45a-45d are uninsulated to allow an electrical current to be communicated to the heart tissue 15 in which the electrode distal end 35a-35d is implanted.

In one embodiment, the diameter of the body 50a, 50b, 50c, 50d of each electrode 10a, 10b, 10c, 10d is less than or equal to approximately three French. In one embodiment, the diameter of the body 50a, 50b, 50c, 50d of each electrode 10a, 10b, 10c, 10d is approximately one French.

The needle 110 includes a lumen 115, a distal end 120 and a proximal end 125. The electrodes 10a, 10b, 10c, 10d are staged within the lumen 115 of the needle 110 in a series arrangement such that the distal end 35a of the first or leading electrode 10a is the most distally positioned, respectively followed by the distal ends 35b, 35c, 35d of the second, third and fourth electrodes 10b, 10c, 10d. Accordingly, the electrodes 10a-10d are positioned within the lumen 115 of the needle 110 such that the electrodes 10a-10d can be implanted in different locations along the surface 30 of the heart wall tissue 15 in the order of their series staging arrangement in the lumen 115 of the needle 110. While four electrodes 10a-10d are depicted in FIGS. 17-21 as being staged within the lumen 115 of the needle 110, in other embodiments a greater or lesser number of electrodes 35 will be staged within the lumen 115.

Each electrode 10a-10d is longitudinally displaceably positioned in the lumen 115 of the needle 110. More specifically, as will be discussed later in this Detailed Description with respect to FIGS. 25 and 26, the electrodes 10a-10d are adapted to displace distally as a group with the needle 110, but are adapted such that the needle 110 and the non-implanted electrodes 10b-10d can be proximally displaced as a group while leaving behind the implanted electrode 10a. The needle 110 is longitudinally displaceably positioned in the lumen 40 of the catheter 25.

As depicted in FIG. 17, the distal end 120 of the needle 110 abuts against a feature of the first electrode 10a. In one embodiment, the first electrode 10a is positioned distal of the distal end 120 of the needle 115 and the feature is the proximal side of one or more of the hook features 45a of the distal end 35a of the first electrode 10a. The remaining staged electrodes 10b-10d are located proximal of the distal end 120 of the needle 110.

As illustrated in FIG. 17, the distal end 20 of the catheter is pushed against the surface 30 of the tissue wall 15 of the heart. In one embodiment, the surface 30 is the epicardium 30 and the catheter distal end 20 approaches the epicardium 30 via the intrapericardial space 65. In one embodiment, the surface 30 is the endocardium 30 and the catheter distal end 20 approaches the endocardium 30 via the endocardial space 65.

As shown in FIG. 18, once the distal end 20 of the catheter 25 is positioned against the surface 30 of the heart tissue wall 15, a distally oriented force is exerted against the needle proximal end 125. Because the needle distal end 120 engages a feature (e.g., one or more of the hook features 45a) of the first electrode 10a and because the electrodes 10a-10d are adapted to displace distally as a group, the distally oriented force causes the needle 110 and the electrodes 10a-10d to distally displace in the catheter lumen 40, which causes the electrode distal end 35a of the first or leading electrode 10a to extend from the catheter lumen 40 and into the heart tissue wall 15 via the piercing tip 60a.

As shown in FIG. 19, in one embodiment, once the distal end 35a of the first or leading electrode 10a has pierced the heart tissue wall 15 a sufficient distance, a proximally oriented force is applied to the needle proximal end 125. The proximally oriented force proximally displaces the needle 110, which causes the needle distal end 120 to withdraw from the electrode feature (e.g., the proximal side of the one or more hook features 45a) of the first electrode 10a.

In one embodiment, as the needle 110 is retracted after the first electrode 10a has sufficiently pierced the heart tissue wall 15, the first electrode 10a is retracted with the needle 110. As a result, the hook feature(s) 45a of the first electrode 10a are caused to imbed in the heart tissue wall 15 to appear as shown in FIG. 20.

Alternatively, in another embodiment, as depicted in FIG. 20, once the needle 110 has fully retracted after the first electrode 10a has sufficiently pierced the heart tissue wall 15, the first electrode 10a is then retracted. As a result, the hood feature(s) 45a of the first electrode 10a are caused to imbed in the heart tissue wall 15.

As shown in FIG. 21, once the needle 110 is fully retracted proximally with the non-implanted electrodes 10b-10d, a distally oriented force is applied to the proximal ends 55b-55d of the remaining non-implanted electrodes 10b-10d to cause the non-implanted electrodes 10b-10d to displace distally within the lumen 115 of the needle 110 until the distal end 35b of the second electrode 10b becomes positioned distal to the distal end 120 of the needle 110. As a result, the needle 110 is now ready to implant the second electrode 10b, and the catheter distal end 20 is placed against the surface 30 of the heart wall tissue 15 at a second electrode implantation location. The process is then repeated to implant the second electrode 10b in the second electrode implantation location. The process continues to be repeated as necessary until each of the electrodes 10a-10d is implanted in its respective implantation location in the heart tissue wall 15 to achieve an electrode implant arrangement that facilitates biventricular pacing.

Figure 24:
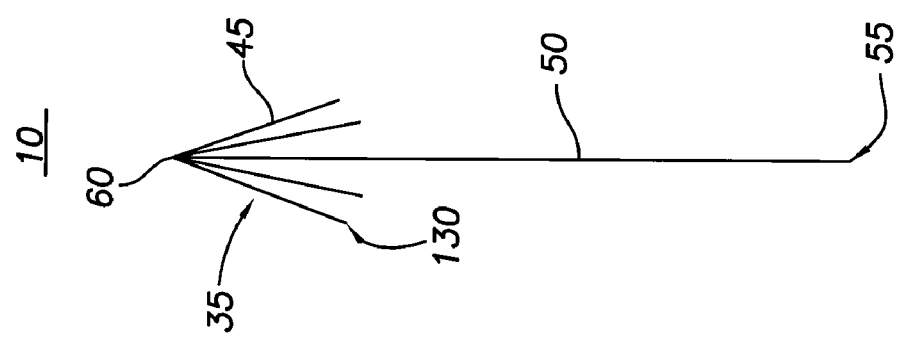
FIG. 24 is a diagrammatic representation of a four-hook feature equipped electrode for a pacing or defibrillation lead.
Figure 23:
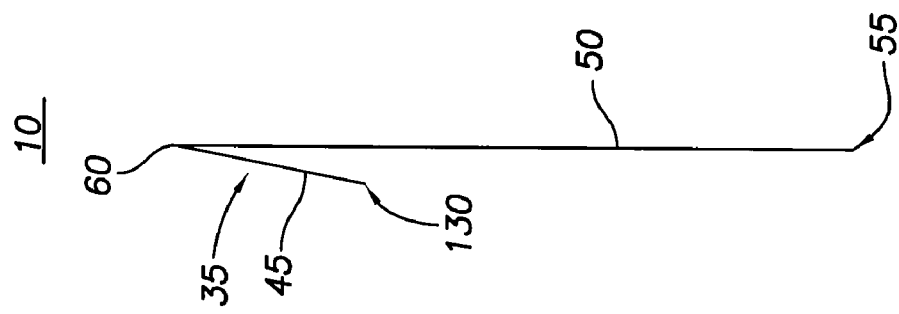
FIG. 23 is a diagrammatic representation of a singe hook feature equipped electrode for a pacing or defibrillation lead.
Figure 22:
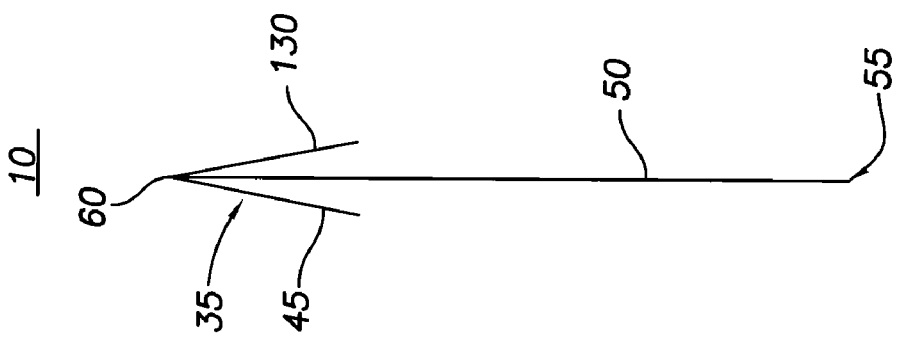
FIG. 22 is a diagrammatic representation of a two-hook feature equipped electrode for a pacing or defibrillation lead.

For a further discussion regarding the electrodes 10 depicted in FIGS. 1-21, reference is made to FIGS. 22-24. FIG. 22 is a diagrammatic representation of a two-hook feature equipped electrode 10 for a pacing or defibrillation lead. FIG. 23 is a diagrammatic representation of a singe hook feature equipped electrode 10 for a pacing or defibrillation lead. FIG. 24 is a diagrammatic representation of a four-hook feature equipped electrode 10 for a pacing or defibrillation lead.

As indicated in FIGS. 22-24, each electrode 10 includes an insulated body 50, a distal end 35 and a proximal end 55. The distal end 35 includes one or more hook features 45 (e.g., barbs, hooks, etc.) and terminates in a piercing tip 60. In one embodiment, the hook features 45 are uninsulated to allow an electrical current to be communicated to the heart tissue 15 in which the electrode distal end 35 is implanted. In one embodiment, the characteristics of the insulated body 50 in combination with the support provided by the walls of the lumen 40 of the catheter 25 will make the electrode 10 sufficiently rigid or stiff to facilitate the electrode's distal displacement through one of the aforementioned lumens 40, 95, 115 depicted in FIGS. 1-21.

In one embodiment, the hook features 45 extend proximally to a free end 130 from a point on the body 50 near the piercing point 60. In other words, the free ends 130 are oriented proximally such that the hook features 45 automatically engage the heart tissue 15 when the electrode 10 is displaced proximally after having the distal end 35 of the electrode 10 penetrated into the heart tissue 15. Although the proximal orientation of the hook features 45 facilitates the distal end 35 of the electrode 10 automatically becoming fixed in the heart tissue 15 upon the electrode 10 being displace proximally, the proximal orientation of the hook features 45 does not interfere with the distal end 35 of the electrode 10 piercing the heart tissue 15 via the piercing point 60 when the electrode 10 is displaced distally. While FIGS. 22-24 depict electrodes 10 having one, two and four hook features 45, other embodiments will have three, five or more hook features 45.

In one embodiment, the diameter of a body 50 of an electrode 10 is less than or equal to approximately three French. In one embodiment, the diameter of a body 50 of an electrode 10 is approximately one French.

Figure 26:
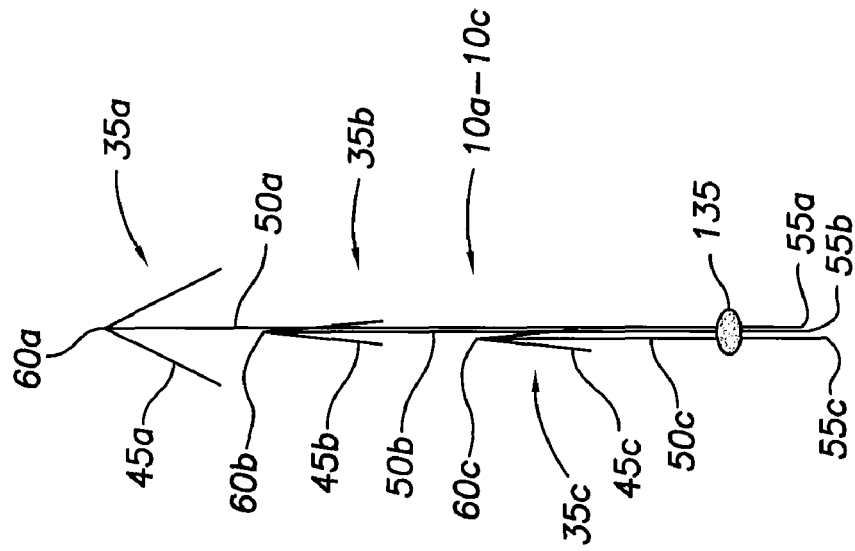
FIG. 26 is the same diagrammatic representation as FIG. 25, except the locking element is set to allow a group of the electrodes to displace relative to a single electrode.
Figure 25:
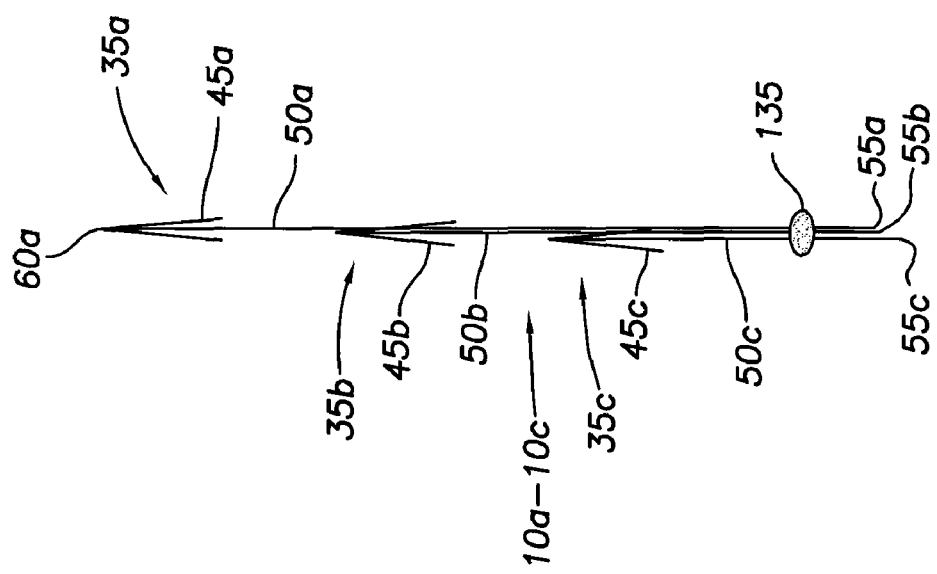
FIG. 25 is a diagrammatic depiction of a series of electrodes provided with an electrode-locking element, wherein the locking element is set to have the electrodes displace as a group.

For a discussion regarding an assembly that allows grouped or selective displacement of the electrodes 10a, 10b, 10c, as described with respect to the embodiments depicted in FIGS. 10-21, reference is made to FIGS. 25 and 26. FIG. 25 is a diagrammatic depiction of a series of electrodes 10a, 10b, 10c provided with an electrode locking element 135, wherein the locking element 135 is set to have the electrodes 10a, 10b, 10c displace as a group. FIG. 26 is the same diagrammatic representation as FIG. 25, except the locking element 135 is set to allow a group of the electrodes 10b, 10c to displace relative to a single electrode 10a.

As can be understood from FIG. 25 and as explained with respect to FIGS. 10-21, the electrodes 10a-10c are placed in a lumen 95, 115 of a push tube 90 or needle 110 in a series spaced arrangement. In one embodiment, a locking element 135 is provided near the distal ends 55a-55c of the electrodes 10a-10c to engage the electrodes 10a-10c and preventing them from displacing relative to each other. Thus, the series arrangement of electrodes 10a-10c can be displaced distally as a group when the distal end 35a of the leading or first electrode 10a is pierced into the heart tissue 15.

As can be understood from FIG. 26 and as explained with respect to FIGS. 10-21, once the leading or first electrode 10a has its distal end 35a fixed in the heart tissue 15 via the hook features 45a, the locking element 135 can be adjusted to allow the non-implanted electrodes 10b, 10c to displace relative to the implanted electrode 10a, or vice versa. Thus, the implanted electrode 10a can be proximally displace relative to the non-implanted electrodes 10b, 10c to set the distal end 35a of the implanted electrode 10a in the heart tissue 15. Also, the locking element 135 allows the implanted electrode 10a to remain undisturbed in the heart tissue 15 as the non-implanted electrodes 10b, 10c are positioned within the push tube 90 or needle 110 to allow the second electrode 10b to be implanted in the heart tissue at a different location as described with respect to FIGS. 10-21.

For each of the embodiments depicted in FIGS. 1-26, the un-insulated portion of the electrode 10 that conducts electrical energy to the heart tissue 15 (e.g., the distal end 35 and hook features 45 of the electrode 10 or some other un-insulated portion of the electrode 10, including the entire electrode 10 if un-insulated in its entirety) is imbedded anywhere in the heart tissue 15. For example, in one embodiment, the un-insulated portion of the electrode 10 that conducts electrical energy to the heart tissue 15 is imbedded transmurally in the heart tissue 15 (e.g., the un-insulated portion of the electrode 10 extends through one or both surfaces of a heart tissue wall). In one embodiment, the un-insulated portion of the electrode 10 that conducts electrical energy to the heart tissue 15 is imbedded intramurally in the heart tissue 15 (e.g., the un-insulated portion of the electrode 10 is located completely within the heart tissue wall such that it does not extend through a surface of a heart tissue wall).

In one embodiment, the un-insulated portion of the electrode 10 that conducts electrical energy to the heart tissue 15 is imbedded anywhere in the heart tissue 15 from the endocardial space to the epicardial space. In one embodiment, the un-insulated portion of the electrode 10 that conducts electrical energy to the heart tissue 15 is imbedded anywhere in the heart tissue 15 across the interatrial septal wall or the interventricular septal wall. In one embodiment, the un-insulated portion of the electrode 10 that conducts electrical energy to the heart tissue 15 is imbedded anywhere in the heart tissue 15 from the pericardial space to the endocardial space.

In one embodiment, the un-insulated portion of the electrode 10 that conducts electrical energy to the heart tissue 15 is imbedded anywhere in the heart tissue 15 from the epicardial space to the myocardium. In one embodiment, the un-insulated portion of the electrode 10 that conducts electrical energy to the heart tissue 15 is imbedded anywhere in the heart tissue 15 from the endocardial space to the myocardium. In one embodiment, the un-insulated portion of the electrode 10 that conducts electrical energy to the heart tissue 15 is imbedded anywhere in the heart tissue 15 from the pericardial space to the myocardium. In one embodiment, the un-insulated portion of the electrode 10 that conducts electrical energy to the heart tissue 15 is imbedded anywhere in the heart tissue 15 from a septal wall to the myocardium.

Although the present invention has been described with reference to preferred embodiments, persons skilled in the art will recognize that changes may be made in form and detail without departing from the spirit and scope of the invention.

What is claimed is:

1. A method of implanting one or more electrodes of a pacing or defibrillation lead in heart tissue, the method comprising:
    positioning a distal end of a catheter against a surface of the heart tissue;
    extending a distal end of a first electrode from a lumen of the catheter, the first electrode configured to conduct electrical energy and including a longitudinally extending portion comprising a proximal end and a distal end, the distal end of the first electrode comprising a piercing tip and at least one hook feature;
    subsequent to said extending, applying an initial axial force along the length of the longitudinally extending portion of the first electrode in the direction of the distal end of the first electrode to thereby cause the piercing tip of the first electrode to pierce the heart tissue, wherein the initial axial force is applied via a push tube positioned within the lumen of the catheter;
    applying a subsequent axial force along the length of the longitudinally extending portion of the first electrode in the direction of the proximal end of the first electrode to thereby retract the first electrode in the proximal direction to thereby fix the hook feature of the first electrode in the heart tissue; and
    extending a distal end of a second electrode from the push tube, the second electrode configured to conduct electrical energy and including a longitudinally extending portion comprising a proximal end and a distal end, the distal end of the second electrode comprising a piercing tip and at least one hook feature, wherein the lumen of the push tube is sized to receive the entire second electrode.

2. The method of claim 1, wherein the heart tissue forms a heart tissue wall having opposed surfaces and the initial axial force is sufficient to cause the piercing tip to pass through both of the opposed surfaces.

3. The method of claim 1, further comprising entering an intrapericardial space with the distal end of the catheter prior to positioning the distal end of the catheter against the surface of the heart tissue.

4. The method of claim 1, further comprising entering an endocardial space with the distal end of the catheter prior to positioning the distal end of the catheter against the surface of the heart tissue.

5. The method of claim 1, wherein the first electrode is sufficiently stiff along its length to penetrate the surface of the heart tissue.

6. The method of claim 1, wherein an un-insulated portion of the first electrode that conducts electrical energy to the heart tissue is imbedded anywhere in the heart tissue across an interatrial septal wall or an interventricular septal wall.

7. The method of claim 1, wherein an un-insulated portion of the first electrode that conducts electrical energy to the heart tissue is imbedded anywhere in the heart tissue from the pericardial space to an endocardial space.

8. The method of claim 1, wherein an un-insulated portion of the first electrode that conducts electrical energy to the heart tissue is imbedded anywhere in the heart tissue from an epicardial space to a myocardium.

9. The method of claim 1, wherein the push tube comprises a lumen and a distal end, the lumen of the push tube sized to receive the longitudinally extending portion of the first electrode, and the distal end of the push tube configured to abut against a feature of the first electrode at the distal end of the first electrode so as to facilitate application of the initial axial force.

10. The method of claim 9, wherein the distal end of the push tube is configured to engage the first electrode so as to facilitate application of the subsequent axial force.

11. The method of claim 1, further comprising, subsequent to said extending of the distal end of the second electrode from the push tube, using the push tube to apply an axial force along the length of the longitudinally extending portion of the second electrode in the direction of the distal end of the second electrode to thereby extend the distal tip of the second electrode from the catheter to cause the piercing tip of the second electrode to pierce the heart tissue.

12. The method of claim 11, further comprising, subsequent to said piercing of the heart tissue by the second electrode, applying a subsequent axial force along the length of the longitudinally extending portion of the second electrode in the direction of the proximal end of the first electrode to thereby retract the second electrode in the proximal direction to thereby fix the hook feature of the second electrode in the heart tissue.

13. An assembly for implanting in heart tissue an electrode of a defibrillation or pacing lead, the assembly comprising:
    a catheter comprising a proximal end, a distal end and a lumen extending between the proximal and distal ends;
    a first electrode displaceably received in the lumen and comprising a longitudinally extending portion comprising a proximal end and a distal end, the distal end of the first electrode comprising a piercing tip and at least one hook feature; and
    a push tube positioned in the lumen of the catheter wherein the push tube comprises a lumen and a distal end, the lumen of the push tube is sized to receive the longitudinally extending portion of the first electrode, and the distal end of the push tube is configured to abut against a feature of the first electrode so as to facilitate movement of the first electrode in a first direction through the distal end of the catheter;
    wherein the application of an axial force along the length of the longitudinally extending portion of the first electrode in the direction of the distal end of the first electrode causes the piercing tip of the first electrode to pierce the heart tissue and a subsequent application of an axial force along the length of the longitudinally extending portion of the first electrode in the direction of the proximal end of the first electrode causes the hook feature to become fixed in the heart tissue; and
    wherein the distal end of the push tube is configured to engage the first electrode so as to facilitate movement of the first electrode in a second direction opposite the first direction.

14. The assembly of claim 13, wherein a body of the first electrode has a diameter of less than or equal to approximately three French.

15. The assembly of claim 13, wherein a body of the first electrode has a diameter of approximately one French.

16. An assembly for implanting in heart tissue an electrode of a defibrillation or pacing lead, the assembly comprising:
    a catheter comprising a proximal end, a distal end and a lumen extending between the proximal and distal ends;
    a first electrode displaceably received in the lumen and comprising a longitudinally extending portion comprising a proximal end and a distal end, the distal end of the first electrode comprising a piercing tip and at least one hook feature; and
    a push tube positioned in the lumen of the catheter wherein the push tube comprises a lumen and a distal end, the lumen of the push tube is sized to receive the longitudinally extending portion of the first electrode, and the distal end of the push tube is configured to abut against a feature of the first electrode at the distal end of the first electrode so as to facilitate movement of the first electrode in a first direction through the distal end of the catheter;
    wherein the application of an axial force along the length of the longitudinally extending portion of the first electrode in the direction of the distal end of the first electrode causes the piercing tip of the first electrode to pierce the heart tissue and a subsequent application of an axial force along the length of the longitudinally extending portion of the first electrode in the direction of the proximal end of the first electrode causes the hook feature to become fixed in the heart tissue; and
    a second electrode configured to conduct electrical energy and including a longitudinally extending portion comprising a proximal end and a distal end, the distal end of the second electrode comprising a piercing tip and at least one hook feature, wherein the lumen of the push tube is sized to receive the entire second electrode.

17. The assembly of claim 16, wherein the piercing tip and at least one hook of the second electrode are proximal the piercing tip and at least one hook of the first electrode.

18. The assembly of claim 16, wherein the second electrode is displaceable within the lumen of the push tube such that the distal end of the second electrode may be positioned distal the distal end of the push tube.

19. An assembly for implanting in heart tissue an electrode of a defibrillation or pacing lead, the assembly comprising:
    a catheter comprising a proximal end, a distal end and a lumen extending between the proximal and distal ends;
    a first electrode displaceably received in the lumen and comprising a longitudinally extending portion comprising a proximal end and a distal end, the distal end of the first electrode comprising a piercing tip and at least one hook feature; and
    a push tube positioned in the lumen of the catheter wherein the push tube comprises a lumen and a distal end, the lumen of the push tube is sized to receive the longitudinally extending portion of the first electrode, and the distal end of the push tube is configured to abut against a feature of the first electrode at the distal end of the first electrode so as to facilitate movement of the first electrode in a first direction through the distal end of the catheter;

wherein the application of an axial force along the length of the longitudinally extending portion of the first electrode in the direction of the distal end of the first electrode causes the piercing tip of the first electrode to pierce the heart tissue and a subsequent application of an axial force along the length of the longitudinally extending portion of the first electrode in the direction of the proximal end of the first electrode causes the hook feature to become fixed in the heart tissue; and a plurality of additional electrodes, each configured to conduct electrical energy and including a longitudinally extending portion comprising a proximal end and a distal end, the lumen of the push tube is sized to receive the additional electrodes in a serial arrangement, wherein the distal end of the first electrode is most distally positioned, respectively followed by the distal ends of the additional electrodes.

* * * * *